United States Patent
Shih et al.

(10) Patent No.: US 7,632,959 B2
(45) Date of Patent: Dec. 15, 2009

(54) THIOCARBONYLTHIO COMPOUND AND FREE RADICAL POLYMERIZATION EMPLOYING THE SAME

(75) Inventors: Kuo Chen Shih, Kaohsiung (TW); Po Wen Chung, Kaohsiung (TW); Mei Hua Wang, Jhunan Township, Miaoli County (TW)

(73) Assignee: Industrial Technology Research Institute, Hsinchu (TW)

( * ) Notice: Subject to any disclaimer, the term of this patent is extended or adjusted under 35 U.S.C. 154(b) by 140 days.

(21) Appl. No.: 11/136,005

(22) Filed: May 24, 2005

(65) Prior Publication Data

US 2006/0270867 A1 Nov. 30, 2006

(51) Int. Cl.
*C07C 327/02* (2006.01)
(52) U.S. Cl. ..................................... 558/230
(58) Field of Classification Search ............... 558/230
See application file for complete search history.

(56) References Cited

OTHER PUBLICATIONS

Lim et al. "Sulfur-Containing Compounds From *Scorodocarpus borneensis* and Their Antimicrobial Activity" Phytochemistry, 1998, vol. 48, No. 5, pp. 787-790.*
Delduc et al. "A Convenient Source of Alkyl and Acyl Radicals" J. Chem. Soc., Chem. Commun. 1988, pp. 308-310.*
Bertrand et al. "A Xanthate Transfer Radical Process for the Introduction of the Trifluoromethyl Group" Organic Letters, 2001, vol. 3, No. 7, pp. 1069-1071.*

* cited by examiner

*Primary Examiner*—Rei-Tsang Shiao
*Assistant Examiner*—Joseph R Kosack
(74) *Attorney, Agent, or Firm*—Thomas, Kayden, Horstemeyer & Risley

(57) ABSTRACT

A thiocarbonylthio compound and free radical polymerization employing the same. The thiocarbonylthio compound is represented by formula (I) or (II):

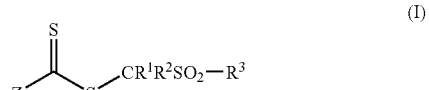

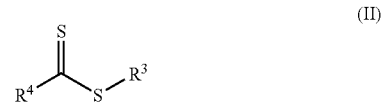

wherein Z can be independently perfluoroalkyl, alkyl, haloalkyl, aryl, alkylaryl, haloalkylaryl, arylalkyl, aminoalkyl, alkylamino, alkoxy, alkoxyaryl, alkylsulfonyl, alkylsulfonylaryl, dialkylphosphinyl, or dialkylphosphinothioyl; $R^1$ and $R^2$ can be each independently hydrogen, alkyl, aryl, alkylaryl, arylalkyl, aminoalkyl, alkylamino, alkoxy or alkoxyaryl; $R^3$ is alkyl, aryl, aminoalkyl, alkylamino, alkoxy or alkoxyaryl. Furthermore, R can also be alkyl, aryl, alkylaryl, arylalkyl, aminoalkyl, alkylamino, alkoxy, haloalkylaryl, alkylsilyl, alkylthio, alkylthioaryl, or substituent contaning CN, CO, COOH, COOCH$_3$ or heterocyclic moieties; and $R^4$ is perfluoroalkyl. The thiocarbonylthio compound can be used as a reversible chain transfer agent in a free radical polymerization to obtain a polymer with a controlled molecular weight and narrow polydispersity.

2 Claims, No Drawings

THIOCARBONYLTHIO COMPOUND AND FREE RADICAL POLYMERIZATION EMPLOYING THE SAME

BACKGROUND

The present invention relates to a thiocarbonylthio compound, and more particularly to a radical polymerization process for preparing polymers of vinyl monomers with controlled molecular weight and narrow polydispersity in the presence of the thiocarbonylthio compound.

Radical polymerization is one of the most widely exploited polymerization processes in industry due to the variety of the polymerizable monomers (such as styrenes, acrylates, methyl methacrylates (MMA) or acrylonitrile (AN)), relatively simple reaction conditions. In conventional radical polymerization, however, it is difficult to control the size of the polymer chains and the molecular mass distribution. The polymers thus prepared contain chains of very large and very small masses (broad polydispersity), and this results in materials with uncontrolled properties.

The traditional living cationic and anionic polymerization methods can be used to control the degree of polymerization for specific monomers and obtained narrow distribution of molecular weight. However, they are limited in their ability to precisely modify the configuration of polymer products. As well, the variety of monomers applied to the above polymerization methods is limited, and strict reaction conditions thereof also restrict use in related applications.

In 1998, CSIRO disclosed a living free radical polymerization method called reversible addition-fragmentation chain-transfer process (RAFT process) to prepare polymer products with narrow molecular weight distribution and further control the polymer chain length. The so-called RAFT process is a combination of general procedures for traditional free radical polymerizations with the addition of a reversible addition-fragmentation chain transfer reagent (RAFT reagent). The conventional RAFT reagents are difficult to prepare and have high cost, due to complex preparation and purification steps.

Therefore, it is necessary to develop a novel radical polymerization process.

SUMMARY

Embodiments of the invention provide a thiocarbonylthio compound, having advantages of easy preparation and simple purification, represented by formula (I) or (II):

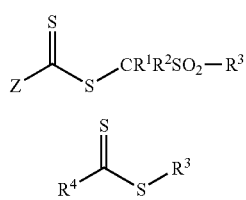

wherein

Z can be independently perfluoroalkyl, alkyl, haloalkyl, aryl, alkylaryl, haloalkylaryl, arylalkyl, aminoalkyl, alkylamino, alkoxy, alkoxyaryl, alkylsulfonyl, alkylsulfonylaryl, dialkylphosphinyl, or dialkylphosphinothioyl;

$R^1$ and $R^2$ can be each independently hydrogen, alkyl, aryl, alkylaryl, arylalkyl, aminoalkyl, alkylamino, alkoxy or alkoxyaryl;

$R^3$ is alkyl, aryl, aminoalkyl, alkylamino, alkoxy or alkoxyaryl. Furthermore, R can also be alkyl, aryl, alkylaryl, arylalkyl, aminoalkyl, alkylamino, alkoxy, haloalkylaryl, alkylsilyl, alkylthio, alkylthioaryl, or substituent contaning CN, CO, COOH, COOCH$_3$ or heterocyclic moieties; and $R^4$ is perfluoroalkyl.

In embodiments of the invention, at least one hydrogen atom bonded to the carbon atom of $R^3$ is substituted optionally by

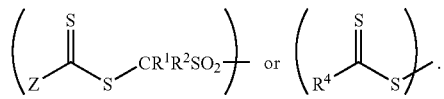

Embodiments of the invention further provide a radical polymerization process comprising polymerizing at least one kind of vinyl monomer in the presence of the above thiocarbonylthio compound. The vinyl monomer can be acrylic acid and its salts, acrylates, methacrylic acid and its salts, methacrylates, acrylonitriles, styrenes, acrylamides, butadiene, isoprene or mixtures thereof.

DETAILED DESCRIPTION

The thiocarbonylthio compound according to embodiments of the invention can be represented by formula (I) or (II):

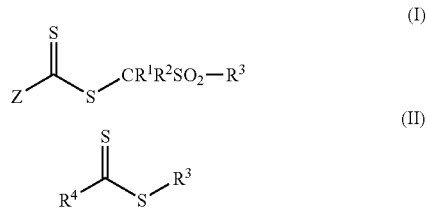

wherein

Z can be independently perfluoroalkyl, alkyl, haloalkyl, aryl, alkylaryl, haloalkylaryl, arylalkyl, aminoalkyl, alkylamino, alkoxy, alkoxyaryl, alkylsulfonyl, alkylsulfonylaryl, dialkylphosphinyl, or dialkylphosphinothioyl;

$R^1$ and $R^2$ can be each independently hydrogen, alkyl, aryl, alkylaryl, arylalkyl, aminoalkyl, alkylamino, alkoxy or alkoxyaryl;

$R^3$ can be alkyl, aryl, aminoalkyl, alkylamino, alkoxy or alkoxyaryl. Furthermore, R can also be alkyl, aryl, alkylaryl, arylalkyl, aminoalkyl, alkylamino, alkoxy, haloalkylaryl, alkylsilyl, alkylthio, alkylthioaryl, or substituent contaning CN, CO, COOH, COOCH$_3$ or heterocyclic moieties. Furthermore, at least one hydrogen atom bonded to the carbon atom of $R^3$ can be substituted optionally by

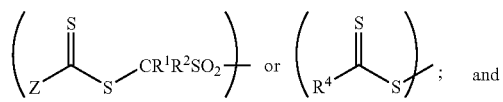

$R^4$ can be perfluoroalkyl.

Alkyl referred to in the present invention can be straight or branched and have 1 to 18, and preferably from 1 to 10, carbonatoms, suchas methyl, ethyl, propyl, orbutyl.

Haloalkyl can be straight or branched and have 1 to 18, and preferably from 1 to 10, carbon atoms, such as chloromethyl (—CH$_2$Cl). Aryl may have 6 to 10 carbon atoms, such as phenyl. Alkylaryl or arylalkyl may have 7 to 20, and preferably from 7 to 15, carbon atoms. An example of alkylaryl is methylphenyl (—C$_6$H$_4$—CH$_3$), and an example of arylalkyl is phenylmethyl (—CH$_2$—C$_6$H$_5$). Haloalkylaryl may have 7 to 20, and preferably from 7 to 15, carbon atoms. An example of haloalkylaryl is trifluoromethylphenyl.

Aminoalkyl referred to in the present invention may contain from 1 to 18, and preferably from 1 to 10, carbon atoms. The aminoalkyl may be primary, secondary, or tertiary. Examples include aminomethyl (—CH$_2$—NH$_2$), methylaminomethyl (—CH$_2$—NH (CH$_3$)), and dimethylaminomethyl (—CH$_2$—N(CH$_3$)$_2$).

Alkylamino referred to in the present invention may contain from 1 to 18, and preferably from 1 to 10 carbon atoms. The alkylamino may be secondary or tertiary. Examples include methylamino (—NH—CH$_3$) and dimethylamino (—N(CH$_3$)$_2$).

Alkoxy referred to in the present invention can be straight or branched and have 1 to 18, and preferably from 1 to 10, carbon atoms. Examples include methoxy and ethoxy. Alkoxyaryl referred to in the present invention may contain from 7 to 24, and preferably from 7 to 16 carbon atoms such as methoxyphenyl.

Alkylthio may contain from 1 to 18, and preferably from 1 to 10, carbon atoms. An example is methylthio (—S—CH$_3$). Alkylsilyl may contain from 1 to 20, and preferably from 1 to 10, carbon atoms. Examples include trimethylsilyl (—Si(CH$_3$)$_3$), dimethylsilyl (—SiH(CH$_3$)$_2$), and dimethylethylsilyl (—Si(CH$_3$)$_2$(C$_2$H$_5$)).

In an embodiment of the present invention, the thiocarbonylthio compound can be represented by formula (III):

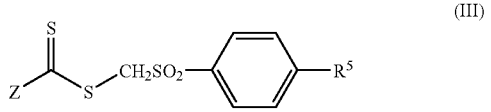

(III)

wherein

Z can be perfluoroalkyl, alkyl, haloalkyl, aryl, alkylaryl, haloalkylaryl, arylalkyl, aminoalkyl, alkylamino, alkoxy, alkoxyaryl, alkylsulfonyl, alkylsulfonylaryl, dialkylphosphinyl, or dialkylphosphinothioyl; and R$^5$ can be hydrogen, alkyl, alkoxy, haloalkyl or alkylthio.

In another embodiment of the present invention, the thiocarbonylthio compound can be represented by formula (IV):

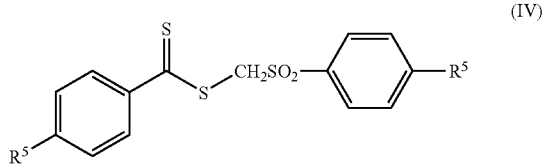

(IV)

wherein

Z can be perfluoroalkyl, alkyl, haloalkyl, aryl, alkylaryl, haloalkylaryl, arylalkyl, aminoalkyl, alkylamino, alkoxy, alkoxyaryl, alkylsulfonyl, alkylsulfonylaryl, dialkylphosphinyl, or dialkylphosphinothioyl; and R$^5$ can be each independently hydrogen, methyl, methoxy, or trifluoromethyl.

According to embodiments of the present invention, the thiocarbonylthio compound can be

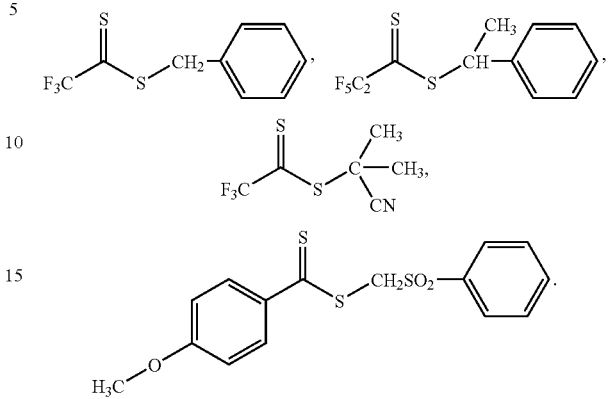

In embodiments of the present invention, the thiocarbonylthio compound can be represented by formula (V) or (VI):

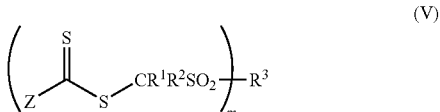

(V)

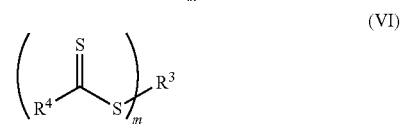

(VI)

wherein m is an integer of 1 to 10, it means

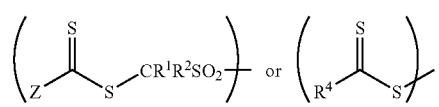

can be optionally bonded to the carbon atom of R$^3$ to substitute for the optional hydrogen atom;

Z can be independently perfluoroalkyl, alkyl, haloalkyl, aryl, alkylaryl, haloalkylaryl, arylalkyl, aminoalkyl, alkylamino, alkoxy, alkoxyaryl, alkylsulfonyl, alkylsulfonylaryl, dialkylphosphinyl, or dialkylphosphinothioyl;

R$^1$ and R$^2$ can each independently be hydrogen, alkyl, aryl, alkylaryl, arylalkyl, aminoalkyl, alkylamino, alkoxy or alkoxyaryl;

R$^3$ can be alkyl, aryl, aminoalkyl, alkylamino, alkoxy or is alkoxyaryl. Furthermore, R can also be alkyl, aryl, alkylaryl, arylalkyl, aminoalkyl, alkylamino, alkoxy, haloalkylaryl, alkylsilyl, alkylthio, alkylthioaryl, or substituent contaning CN, CO, COOH, COOCH$_3$ or heterocyclic moieties; and R$^4$ can be perfluoroalkyl.

The method of preparing thiocarbonylthio compound represented by formula (V) or (VI) refers to the reactions as shown below.

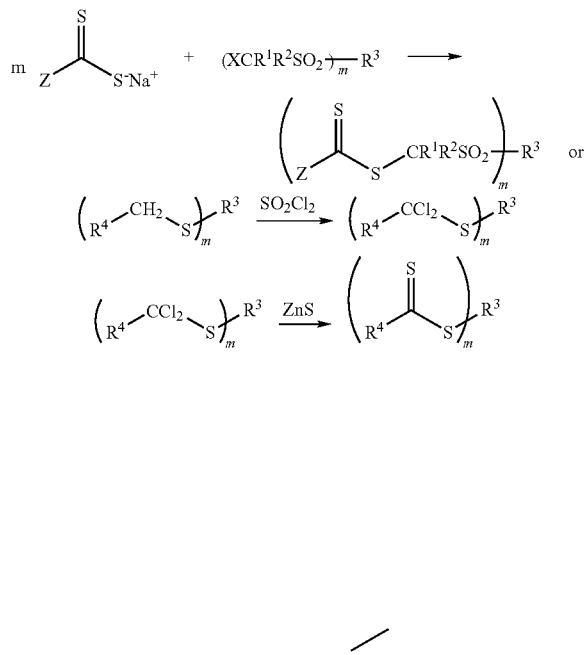

wherein

X is halogen; and m, Z, R1, R2, R3, and R4 are defined as above.

Embodiments of the present invention provide a radical polymerization process, comprising polymerizing at least one kind of monomer in the presence of the above thiocarbonylthio compound.

The monomer can be one vinyl monomer alone, or in combination with one or more polymerizable vinyl comonomers.

Specific monomers include the following:

acrylic acid and its salts, acrylates, methacrylic acid and its salts, methacrylates, acrylonitriles, styrenes, acrylamides, butadiene, isoprene or mixtures thereof. Representative examples include methyl acrylate, ethyl acrylate, propyl acrylate (all isomers), butyl acrylate (all isomers), 2-ethylhexyl acrylate, 2-hydroxyethyl acrylate, isobornyl acrylate, acrylic acid, benzyl acrylate, phenyl acrylate, acrylonitrile, styrene, N,N-dimethylaminoethyl methacrylate, methacrylamides, acrylamides, N-isopropyl acrylamide, or methyl methacrylate etc.

In the presence of the above thiocarbonylthio compound, radical polymerization has living characteristics and provides polymers of controlled molecular weight and low polydispersity.

Furthermore, the radical polymerization process can include polymerizing at least one kind of vinyl monomer in the presence of the above thiocarbonylthio compound and a free radical initiator.

The free radical initiator suitable for use in the present invention is not limited and can be any suitable for use in the conventional free radical polymerization, such as peroxide, perester, or azo initiator. The free radical initiator can generate radicals by thermal-decomposition, oxidation-reduction reaction, or irradiation etc. Representative examples include AIBN, 2,2'-azobis(2-cyano-2-butane), dimethyl 2,2'-azobis(methyl isobutyrate), 4,4'-azobis(4-cyanopentanoic acid), 4,4'-azobis(4-cyanopentan-l-ol), 1,1'-azobis (cyclohexanecarbonitrile), 2-(t-butylazo)-2-cyanopropane, 2,2'-azobis[2-methyl-(N)-(1,1)-bis(hydroxymethyl)-2-hydro xyethyl]propionamide, 2,2'-azobis[2-methyl-N-hydroxyethyl)]propionamide, 2,2'-azobis(N,N'-dimethyleneisobutyramidine) dihydrochloride, 2,2'-azobis (2-amidinopropane) dihydrochloride, 2,2'-azobis(N,N'-dimethyleneisobutyramine), 2,2'-azobis (2-methyl-N-[1,1-bis(hydroxymethyl)-2-hydroxyethyl]propionamide, 2,2'-azobis(2-methyl-N-[1,1-bis (hydroxymethyl)ethyl] propionamide), 2,2'-azobis [2-methyl-N-(2-hydroxyethyl) propionamide], 2,2'-azobis(isobutyramide)dihydrate, 2,2'-azobis (2,2,4-trimethylpentane), 2,2'-azobis(2-methylpropane), dilauroyl peroxide, tertiary amyl peroxides, tertiary amyl peroxydicarbonates, t-butyl peroxyacetate, t-butyl peroxybenzoate, t-butyl peroxyoctoate, t-butyl peroxyneodecanoate, t-butylperoxy isobutyrate, t-amyl peroxypivalate, t-butyl peroxypivalate, di-isopropyl peroxydicarbonate, dicyclohexyl peroxydicarbonate, dicumyl peroxide, dibenzoyl peroxide, potassium peroxydisulfate, ammoniumperoxydisulfate, di-tert butyl peroxide, di-t-butyl hyponitrite, or dicumyl hyponitrite.

The molar ratio of the free radical initiator to the thiocarbonylthio compound can be from 10:1 to 1:10, more preferably 5:1 to 1:5, and most preferably 2:1 to 1:5.

The polydispersity index (PDI) of the polymer obtained is usually in a range from 1.05 to 2.5, and preferably decreased to a range from 1.05 to 1.5, and more preferably decreased to a range from 1.05 to 1.3.

Using the present invention, the polymer obtained can be a homopolymer or a copolymer. Various polymers with a well-defined structure can be obtained, including (1) block copolymers (two or more blocks) with narrow polydispersity, (2) graft copolymers with narrow polydispersity, (3) gradient copolymers, (4) star (co-)polymers, and (5) hyperbranched (co-)polymers. Various polymers with a terminal functional group can also be prepared. The emergence of various novel polymers can provide new materials with new physical properties to be applied in industry. This will not only enhance the performance of the existing products, but also speed up the development of new products. The polymeric materials developed in the present invention can be applied in many fields, including dispersants such as pigment dispersants in ink, color filter, photoresists, surfactants, surface treating agents, adhesives, rheology controllers, coatings, and thermoplastic elastomers.

The following examples are intended to demonstrate this invention more fully without limiting its scope, since numerous modifications and variations will be apparent to those skilled in the art.

Synthesis of Thiocarbonylthio Compound

EXAMPLE 1

Preparation of Thiocarbonylthio Compound (I)

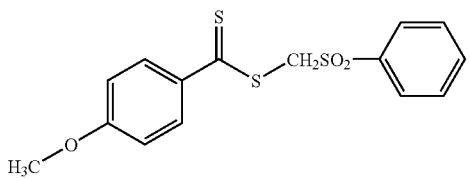

To a mixture of methanol (15 mL), sulfur (0.06 mol, 1.92 g) and sodium methoxide solution (30% in methanol, 12 mL), was added dropwise p-methoxybenzyl chloride (0.03 mol, 3.8 g) within one hour. The reaction mixture was allowed to heat and stirred at 70° C. for 3 hours. After cooling to room temperature, the resulting dithiobenzoic acid salt was dissolved in acetonitrile (200 ml). Bromomethylphenyl sulfone was added and the reaction mixture was heated to reflux for 6 hours with stirring. After cooling, filtering, and removing the volatiles in vacuum, the residue was subjected to purification by column chromatography from a mixed solvent (EA:hexane=2:3) and to recrystallization from acetone/hexane, giving thiocarbonylthio compound (I).

The reaction according to Example 1 is shown below.

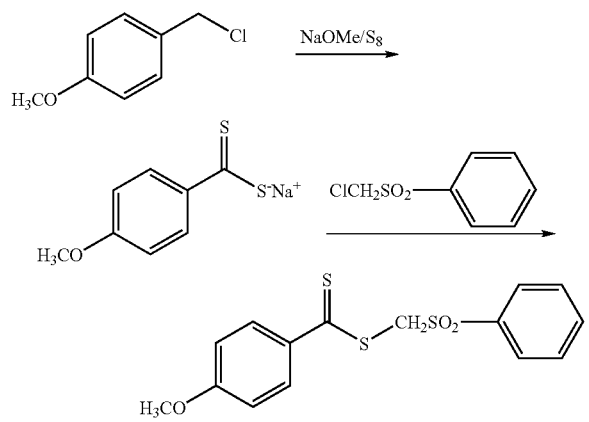

EXAMPLE 2

Preparation of Thiocarbonylthio Compound (II)

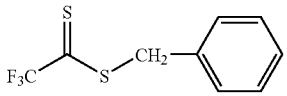

$SO_2Cl_2$ (0.02 mol) dissolved in 10 mL $CH_2Cl_2$ was added dropwise benzyl(2,2,2-trifluoroethyl)sulfide (0.01 mol) dissolved in 20 mL $CH_2Cl_2$. After stirring 3 hours at room temperature, $CH_2Cl_2$ of the mixture was removed in vacuum (0.2 torr) at room temperature, giving benzyl(1,1-dichloro-2,2,2-trifluoroethyl)sulfide as a yellow liquid. benzyl(1,1-dichloro-2,2,2-trifluoroethyl)sulfide (0.008 mol) and ZnS (0.16 mol) was dissolved in acetonitrile (16 ml), and the mixture was heated to reflux for 12 hours. After cooling to room temperature and filtering, the residue was subjected to purification, giving thiocarbonylthio compound (II).

The reaction according to Example 2 is shown below.

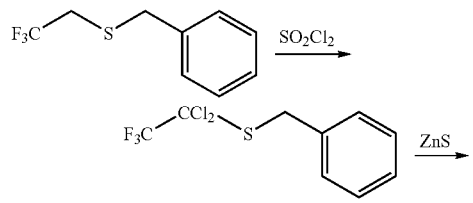

-continued

Synthesis of Polymer with Low Polydispersity Index

EXAMPLE 3

Preparation of Low Polydispersity Poly (t-butyl acrylate) Using Thiocarbonylthio Compound (I)

T-Butyl acrylate (5 mL), toluene (2.5 mL), azobisisobutyronitrile (6.2 mg) and thiocarbonylthio compound (I) (26 mg) were placed in a Schlenk tube. The solution was degassed through four freeze-pump-thaw cycles prior to being heated at 60° C. for 16 h. The conversion based on the weight of the polymer obtained is 70%. $M_n$ is 39814, and PDI is 1.18.

EXAMPLE 4

Preparation of Low Polydispersity Poly(Styrene) Using Thiocarbonylthio Compound (I)

Styrene (5 mL), toluene (2.5 mL), azobisisobutyronitrile (7.2 mg), and thiocarbonylthio compound (I) (30 mg)) were placed in a Schlenk tube, degassed through four freeze-pump-thaw cycles and polymerized at 60° C. for 16 h. The conversion based on the weight of the polymer obtained is 60%. $M_n$ is 35715, and PDI is 1.26.

EXAMPLE 5

Preparation of Low Polydispersity Poly(Methyl Acrylate) Using Thiocarbonylthio Compound (I)

Methyl acrylate (5 mL), toluene (2.5 mL), azobisisobutyronitrile (7.8 mg), and thiocarbonylthio compound (I) (26 mg) were placed in a Schlenk tube, degassed through four freeze-pump-thaw cycles and polymerized at 60° C. for 15 h. The conversion based on the weight of the polymer obtained is 92%. $M_n$ is 59886, and PDI is 1.19.

EXAMPLE 6

Preparation of Low Polydispersity Poly(t-butyl acrylate) Using Thiocarbonylthio Compound (II)

T-butyl acrylate (3 mL), toluene (1 mL), azobisisobutyronitrile (4.29 mg), and thiocarbonylthio compound (II) (12.5 mg) were placed in a Schlenk tube, degassed through four freeze-pump-thaw cycles and polymerized at 60° C. for 15 h. The obtained poly(t-butyl acrylate) has $M_n$ of 59886, and PDI of 1.19.

COMPARATIVE EXAMPLE 1

The same procedures described in Example 3 were performed except that thiocarbonylthio compound (I) was replaced by

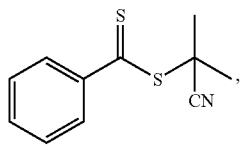

which is a chain transfer agent used in WO 98/01478. The polymer obtained has conversion 47%, $M_n$ 24600, and PDI 1.33, with a high molecular weight shoulder.

The gel permeation chromatography (GPC) analysis of the obtained polymer exhibited not only a major peak but a minor peak (adjacent to the major peak) which was absent in GPC) analysis of the obtained polymer of Example 3. Therefore, the radical polymerization process according to the present invention can prepare a low PDI polymer without bimodal molecular weight distribution.

The thiocarbonylthio compound in embodiments of the present invention has advantages of easy preparation and simple purification. Furthermore, the thiocarbonylthio compound can be served as RAFT reagentsand be employed in free radical polymerization to produce polymers with low polydispersity index. Moreover, the radical polymerization employing the thiocarbonylthio compound can be taken to high conversion with high molecular weight without bimodal molecular weight distribution.

While the invention has been described by way of example and in terms of preferred embodiment, it is to be understood that the invention is not limited thereto. It is therefore intended that the following claims be interpreted as covering all such alteration and modifications as fall within the true spirit and scope of the invention.

What is claimed is:

1. A thiocarbonylthio compound for free radical polymerization represented by formula (IV), of:

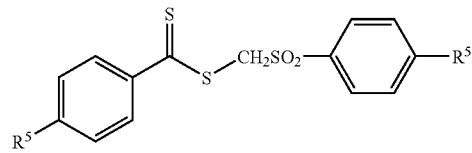

wherein
$R^5$ are each independently hydrogen, methyl, methoxy, or trifluoromethyl.

2. The compound as claimed in claim 1, wherein the thiocarbonylthio compound with the structures represented by formula (IV) is

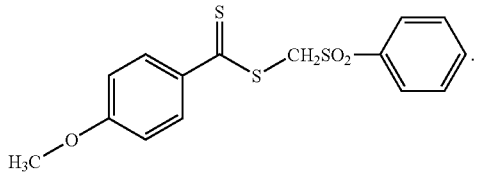

* * * * *

UNITED STATES PATENT AND TRADEMARK OFFICE
CERTIFICATE OF CORRECTION

PATENT NO. : 7,632,959 B2  Page 1 of 1
APPLICATION NO. : 11/136005
DATED : December 15, 2009
INVENTOR(S) : Shih et al.

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 256 days.

Signed and Sealed this

Second Day of November, 2010

David J. Kappos
*Director of the United States Patent and Trademark Office*